United States Patent
Harris et al.

(10) Patent No.: US 6,813,927 B1
(45) Date of Patent: Nov. 9, 2004

(54) LOG TESTING APPARATUS

(75) Inventors: Paul David Harris, Wellington (NZ); Michael Kenneth Andrews, Wellington (NZ)

(73) Assignee: Carter Holt Harvey Limited, Auckland (NZ)

( * ) Notice: Subject to any disclaimer, the term of this patent is extended or adjusted under 35 U.S.C. 154(b) by 0 days.

(21) Appl. No.: 10/030,156

(22) PCT Filed: Jul. 27, 2000

(86) PCT No.: PCT/NZ00/00139

§ 371 (c)(1), (2), (4) Date: Mar. 20, 2002

(87) PCT Pub. No.: WO01/09603

PCT Pub. Date: Feb. 8, 2001

(30) Foreign Application Priority Data

Jul. 30, 1999 (NZ) .................................. 337015
Aug. 10, 1999 (NZ) .................................. 337186

(51) Int. Cl.$^7$ ............................. G01M 7/08; G01N 3/30
(52) U.S. Cl. ..................... 73/12.12; 73/12.09; 73/579
(58) Field of Search ............................ 73/12.12, 12.09, 73/12.01, 579, 580, 581, 582, 583

(56) References Cited

U.S. PATENT DOCUMENTS

| | | | | |
|---|---|---|---|---|
| 3,531,983 A | * | 10/1970 | Heath et al. ................. | 73/584 |
| 4,399,701 A | * | 8/1983 | Dunlop ........................ | 73/579 |
| 4,852,029 A | * | 7/1989 | Pope et al. .................... | 702/41 |
| 4,858,469 A | * | 8/1989 | Hosgood et al. .............. | 73/579 |
| 4,879,752 A | | 11/1989 | Aune et al. .................... | 382/1 |
| 4,926,691 A | | 5/1990 | Franklin et al. ............... | 75/579 |
| 5,097,881 A | * | 3/1992 | Mack .......................... | 144/356 |
| 5,307,679 A | | 5/1994 | Ross ............................ | 73/597 |
| 6,026,689 A | * | 2/2000 | Snyder et al. ................ | 73/602 |
| 6,347,542 B1 | * | 2/2002 | Larsson et al. .............. | 73/12.12 |

FOREIGN PATENT DOCUMENTS

| | | | | |
|---|---|---|---|---|
| DE | 4435975 A1 | 4/1995 | | |
| EP | 0261487 A2 | 3/1988 | | |
| EP | 0403020 A2 | 12/1990 | | |
| JP | 07-103945 | 4/1995 | | |
| JP | 0951006 a | * 9/1997 | .......... | G01N/29/12 |
| JP | 11-064306 | 3/1999 | | |
| NZ | 331527 | 8/1999 | | |
| WO | WO88/10415 | 12/1988 | | |
| WO | WO98/01737 | 1/1998 | | |
| WO | WO99/44059 | 9/1999 | | |
| WO | WO00/36413 | 6/2000 | | |
| WO | WO 01/77669 A1 | * 10/2001 | .......... | G01N/33/46 |
| WO | WO 02/29398 A1 | * 4/2002 | .......... | G01N/29/18 |

* cited by examiner

*Primary Examiner*—Hezron Williams
*Assistant Examiner*—Rose M. Miller
(74) *Attorney, Agent, or Firm*—Jacobson Holman PLLC

(57) ABSTRACT

Apparatus (preferably portable) enabling a felled tree stem or log to have its stiffness characterized. The analysis is performed with best fit recognition procedure or one that emphasizes high harmonics to determine a fundamental frequency related to acoustic speed, which is indicative the stiffness characteristics of the tree stem or log. The apparatus uses a compliantly mounted accelerometer pressed against one end of the tree stem to defect reflections from the other end after impacting the first end. Also disclosed is a method of cutting a stem into logs by establishing a function that represents the nature of speed variation with distance along the stem characteristic for a species and locality. The average speed along a stem and the speed function are used to compute the likely speed at points along the stem, and then the stems are routed for cutting according to their speed.

16 Claims, 10 Drawing Sheets

Figure 1:
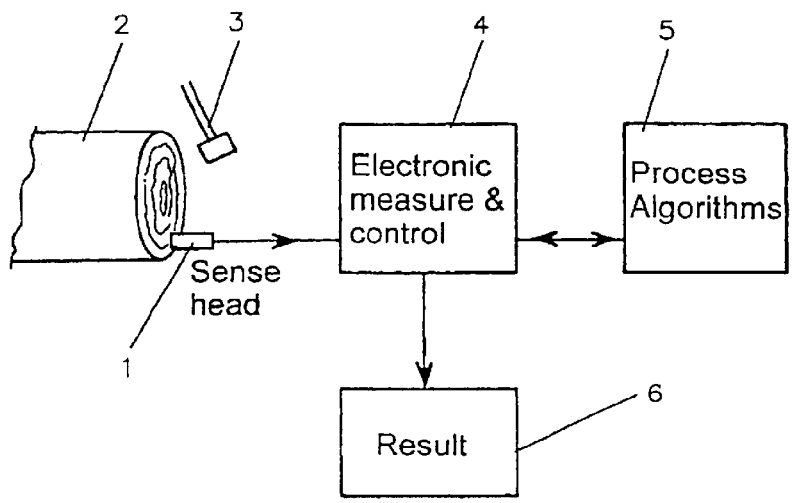

(a) Harmonic series (b) Comb filter generated (c) Spectrum (d) Power in Filter

LOG TESTING APPARATUS

This is a nationalization of PCT/NZ00/00139 filed Jul. 27, 2000 and published in English.

TECHNICAL BACKGROUND

The invention relates to apparatus useful in a method of assessing pulp, paper or wood from the stem of a felled tree (e.g., so as to be determinate of possible destinies of logs to be cut from the stem), such as stiffness of sections of wood cut from the stem, or wood fibre characteristics such as fibre length or the strength of pulp produced from the wood.

BACKGROUND ART

The timber industry faces a need to efficiently utilise its rather variable forest resource. Timber classification, for example machine stress grading, is currently done at the end of the production chain. This process results in wastage from processing which ultimately proves to have been inappropriate. Clearly, it would be more efficient to measure log properties early in the chain and process the logs accordingly.

In our New Zealand Patent Specification Nos. 331527 (filed Aug. 1998) and NZ333434 filed Dec. 17, 1998 there are disclosed procedures in respect of the testing of felled tree stems or logs with a view to determining a destiny for that tree stem or log or logs to be cut from the tree stem.

New Zealand Patent Specification 331527 is directed to the selection of wood according to fibre characteristics so as to determine materials appropriate for the pulp and paper industry whilst, New Zealand Patent Application 333434 is directed to timber or lumber cutting determinations but with the prospects of directing inappropriate tree stems or logs to the pulp and paper industry.

DISCLOSURE OF THE INVENTION

The present invention is directed to apparatus sufficiently portable and effective in usage which will allow the adoption of such aforementioned methods in the field.

It is therefore an object of the present invention to provide such apparatus and the use of such apparatus in the field for such tree stem or log assessment purposes. As used herein MOE is the dynamic modulus of elasticity derived by the product of (A) the square of the velocity of an appropriate wave propagation between the ends of a felled tree stem or a log ($V^2$) and (B) the specimen density $\rho$.

In one aspect the invention consists in an apparatus for providing an indicator of or from which stiffness can be estimated for elongate timber, logs or felled tree stems (hereafter "logs") of known length L or measurable length L, said apparatus comprising or including sensing means capable of being placed in contact with or in close proximity to a log end to detect the impulse and echoes thereof resulting from a striking of the other or that same log end, processing means to derive using an echo or echoes sensed by said sensing means a said indicator, and display means to display said indicator or any derivative thereof received from said processing means, wherein said processing means tests algorithmically frequency transformed data derived from time based echo data with a view to deriving a measure or good estimate of fundamental frequency $f_0$, and wherein L is or can be entered into said processing means, and wherein said processing means derives said indicator by reference to both $f_0$ and L.

Preferably said processing means tests all spectral peaks of the echo data for membership of a series from which a best value of fundamental frequency $f_0$ can be derived and related to the plane wave speed V and specimen length L by $V=2L/f_0$ rather than by reliance on the identification of any single resonance peak.

Preferably said processing means recognises that the characteristic frequencies may be shifted significantly from a harmonic series $f_0, 2f_0, 3f_0, \ldots$ set and recognises that a better indication of the fundamental frequency $f_0$, from which the speed V can be found is obtained from higher harmonics.

Preferably said processing means recognises that a better indication of the fundamental frequency $f_0$ than an attempted direct measure of $f_0$ itself is from at least the second harmonic.

Preferably said processing means recognises that whilst the natural resonance frequencies of stems and logs may be far from harmonic (principally on account of the asymmetry introduced by their taper or loading eg; when stacked) they may be transformed to a harmonic series by applying a correction which decreases as the harmonic number increases.

Preferably said processing means can transform observed resonant frequencies $f_n$ into multiples of a "true" fundamental frequency $f_0$ from which a plane wave velocity can be derived by reliance upon the relationship $(f_n=n\ f_0)/f_n=kc^{-n}$.

Preferably said the fractional deviation falls in geometric progression with ratio approximately 2.7.

Preferably the relationship is $f_n/nf_0-1=k/n^2$.

Preferably said processing means discriminates against noise spikes in the spectra, peaks from unwanted modes inadvertently excited, or any other signals which differ from the spectral peaks sought and which have the desired relationship by using a comb filter comprising a number of frequencies ("centre" frequencies) which match the sought relationship, which can themselves be harmonic or have some other relationship, the comb filter having passbands wide enough to allow small derivations about each centre frequency.

forming the sum of the products of the actual spectral peaks and the comb filter, and identifying as the sequence or filter which accounts for most spectral power, and, where necessary.

deciding between two filters which produce equal power sums on the basis of the comb which produces the least frequency offset between the actual spectral peaks and the filter centre frequencies.

Preferably said processing means uses such transforms to convert a harmonic series with a defined base frequency $f_0$ to a non-harmonic series, thereby defining the centre frequencies of a comb filter with which the actual series may be compared, without the need for all members of the actual series to be present.

Preferably said processing means can calculate a confidence number to be displayed by said display means to indicate the likelihood that the indicated velocity is correct or whether a re-measure is advisable based on the amount of power in the spectral peak series identified with a base value of $f_0$, compared with spectral power not accounted for, e.g. that assumed to be in spurious noise spikes or non-longitudinal resonances inadvertently excited.

Preferably said indicator is V or $V^2$ or a function of V or a function of $V^2$.

Preferably said indicator is $V^2$ or a function of $V^2$ derived from a value or function of V, V having been determined by $V=2L f_n$.

Preferably said display means displays $V^2$ or an indicator or indicators of the one or more properties being assessed, such as MOE or an approximation of MOE derived from $MOE=\rho V^2$ where $\rho$ has been approximated (e.g. as near 1000 kg/m$^3$ for green felled logs).

Preferably said sensing means and/or processing means includes amplification means to ensure a sufficient gain to ensuing echoes in use.

Preferably said sensing means is adapted to be placed in contact with said log end.

Preferably said sensing means carries a switch for said processing means conducive, when activated, of good log/sensing means contact.

Preferably said sensing means is compliantly mounted by a sensing head to be physically pressed by a user against the log surface to be tested.

Preferably the compliant mounting of said sensing means within the means to be handled by a user i.e. the sensing head, is compliantly mounted by use of silicone rubber.

Preferably said sensing means is in a sensing head connected by flexible means to apparatus carrying said processing means and said display means.

Preferably said sensing means is or includes a piezo-style accelerometer.

Preferably said processing means has analog signal acquisition means, means for digitization and processing into a characteristic spectrum of the acquired analog signal data of the echoes and further software algorithms to interpret the data.

Preferably, with a view to power saving, said display means is a small low power display.

Preferably said sensing means is in a sensing head capable of one handed manipulation by a user and whereby the apparatus is adapted to minimise power consumption by allowing initiation of the measurement sequence by finger pressure on a push switch immediately prior to the striking of a log to be tested, such pressure on such a push switch encouraging positive contact between the head and the log surface.

Preferably said processing means is adapted to threshold the signal from said sensing means and immediately to apply an exponentially increasing amplification of the signal to compensate for absorption of the signal in the log so increasing the time over which acoustic signals can be useful digitalised and to increase spectral resolution.

Preferably the apparatus is such that power consumption is adapted to be minimised by allowing operation under the control of PLDs which remain in low current mode until enabled by an initiation switch after which there is a powering up, at least as needed, of analogue functions of said processing means with respect to signal acquisition, powering up and analysis of such signals and a sending results to the display means before being subsequently powered down after a time period or time periods.

Preferably there is provided a keyboard through which data entries can be made into said processing means.

Preferably preset information for data entry is selected from the class any one or more of (i) velocity class codes e.g. colours to be painted on a log after its speed group is determined, (ii) log length codes, (iii) information analysis purposes, (iv) information for instrument configuration purposes, and/or (v) to control the sending of spectral information via a serial port to an external computer for graphical display or archiving.

Preferably, if desired, the apparatus can be externally controlled e.g. by connecting an external device via a serial port to the instrument power controllers and its microprocessor.

Preferably the apparatus has a hardware architecture substantially as herein described with reference to the accompanying drawings and which is operable in a manner substantially as herein described with reference to any one or more of the accompanying drawings.

Preferably said sensing means is adapted to be placed at or in close proximity to the same log end as that to be struck to provide said impulse.

In another aspect the invention is a method of providing an indicator of or from which stiffness, fibre characteristics or other properties can be estimated, which method involves an operative use of apparatus of the present invention.

Preferably said method is performed substantially as herein described with or without reference to any one of the accompanying drawings.

In still a further aspect the invention consists in a method of providing an indicator of or from which stiffness, fibre characteristics, or other properties can be estimated for a felled log of known or measurable length L, said method comprising or including the steps of striking an end of the felled log whilst having sensing means of the previously defined apparatus in contact with or in close proximity to a log end to detect at least one echo of the impulse resulting from the striking of that same or the other log end, processing the output of at least said sensing means in said processing means to derive, using an echo or echoes sensed by said sensing means, a said indicator, and displaying on or by said display means said indicator or any derivative thereof received from said processing means, optionally thereafter appropriately marking or otherwise indicating the fate of the log on the basis of the displayed indicator, said process being further characterised in that said processing means tests frequency transformed data derived from time based echo data with a view to deriving a measure or good estimate of fundamental frequency $f_0$, L is or can be entered into said processing means, and said processing means derives said indicator by reference to both $f_0$ and L.

Preferably said indicator is an estimation of MOE for a green felled log on the basis of an estimation of its density at or about 1000 kg/m$^3$.

In another aspect the invention is the use of apparatus of the present invention for use in a method of the present invention.

In still another aspect the invention is a method of generating and displaying an indicator of stiffness or fibre characteristics of wood within an elongate wooden structure (e.g. a log) which comprises or includes (i) presenting an accelerometer based sensing means compliantly to an end of the elongate wooden structure, (ii) impacting that said end of the structure so as to generate an impulse capable of reflection from the other end thereof, (iii) passing the analogue signal detected by said compliant sensing means to a processing means, (iv) processing the input data in said processing means to generate said indicator, and (v) passing to the display means the generated indicator from said processing means for display, wherein the architecture of the apparatus is such that said sensing means is a sensing head in which said accelerometer is compliantly mounted and is connected by a flexible link to a housing carrying said processing means and said display means.

Preferably said sensing head has a switch capable of being initiated by applying pressure which is conducive to compliant contact of said accelerometer with the end of said wooden structure.

Preferably said apparatus is apparatus as previously defined.

In another aspect the invention is a method of cutting a stem into logs of predicted speeds based upon the stem speed using the fact that the wave or acoustic speed along a stem has a characteristic variation by (i) establishing an expression, the speed function, which represents the nature of the speed variation with distance along the stem, characteristic for a species and a locality, with one adjustable parameter to allow the variation along individual stems, to be matched, (ii) measuring the average speed along the stem by a method as previously defined and converting this to a stem transit time, (iii) integrating the wave travel time along the stem using the speed function, and altering the adjustable parameter until the integrated time equals the measured stem transit time, and (iv) using the speed function thus established to compute the likely speed at points along the stem, to mark and route logs accordingly.

The present invention in another aspect consists in apparatus for providing an indicator of or from which stiffness can be estimated for a felled log of known length L or measurable length L, said apparatus comprising or including sensing means capable of being placed in contact with a log end to detect the impulse and echoes thereof resulting from a striking of that same log end, processing means to derive using an echo or echoes sensed by said sensing means a said indicator, and display means to display said indicator or any derivative thereof received from said processing means, wherein said processing means tests frequency transformed data derived from time based echo data with a view to deriving a measure or good estimate of fundamental frequency $f_0$, and wherein L is or can be entered into said processing means, and wherein said processing means derives said indicator by reference to both $f_0$ and L.

Preferably said indicator is V or $V^2$ or a function of V or a function of $V^2$.

Preferably said indicator is $V^2$ or a function of $V^2$ derived from a value or function of V, V having been determined by $V=2L f_0$.

Preferably said display means displays $V^2$ or an indicator or indicators of the one or more properties being assessed, such as MOE or an approximation of MOE derived from $MOE=\rho V^2$ here $\rho$ has been approximated (e.g. as near 1000 kg/m$^3$ for green felled logs).

Preferably said sensing means and/or processing means includes amplification means to ensure a sufficient gain to ensuing echoes (preferably logarithmic amplification of subsequent echoes).

Preferably said sensing means carries a switch conducive, when activated, of good log/sensor contact.

The present invention is reliant upon any of the processing procedures hereinafter described with or without reference to any one or more of the accompanying drawings and/or with or without reference to any of the algorithmic processes hereafter described.

Preferably the apparatus with a view to power savings in the field includes hardware incorporating analog signal acquisition means, means for digitization and processing into a characteristic spectrum of the acquired analog signal, further software algorithms to interpret the data, and preferably means to provide a small low power display rather than the full screen of a computer.

Preferably such display is of a MOE or wood fibre characteristics indicator.

Preferably said sensing head (preferably a piezo-style accelerometer) is compliantly mounted on a body, e.g.; using a pad of silicone rubber, and capable of being brought into contact with a tree stem end or log end.

Preferably said sensing head is flexibly connected to the processing means and display means.

Preferably said sensing head includes a test commencement switch or the like.

Preferably said sensing means is substantially as hereinafter described with reference to FIG. 1 of the accompanying drawings.

In a further aspect the present invention consists in a method of providing an indicator of or from which stiffness, fibre characteristics, or other properties can be estimated, which method involves an operative use of apparatus as previously set forth.

In still a further aspect the present invention consists in a method of providing an indicator of or from which stiffness, fibre characteristics, or other properties can be estimated for a felled log of known or measurable length L, said method comprising or including the steps of striking an end of the felled log whilst having sensing means of the previously defined apparatus in contact with the log end to detect at least one echo of the impulse resulting from the striking of that same log end, processing the output of at least said sensing means in said processing means to derive, using an echo or echoes sensed by said sensing means, a said indicator, and displaying on or by said display means said indicator or any derivative thereof received from said processing means, optionally thereafter appropriately marking or otherwise indicating the fate of the long on the basis of the displayed indicator, said process being further characterised in that said processing means tests frequency transformed data derived from time based echo data with a view to deriving a measure or good estimate of fundamental frequency $f_0$, L is or can be entered into said processing means, and said processing means derives said indicator by reference to both $f_0$ and L.

Preferably said indicator is an estimation of MOE for a green felled log on the basis of an estimation of $\rho=1000$ kg/m$^3$.

DETAILED DESCRIPTION OF THE INVENTION

Figure 2:
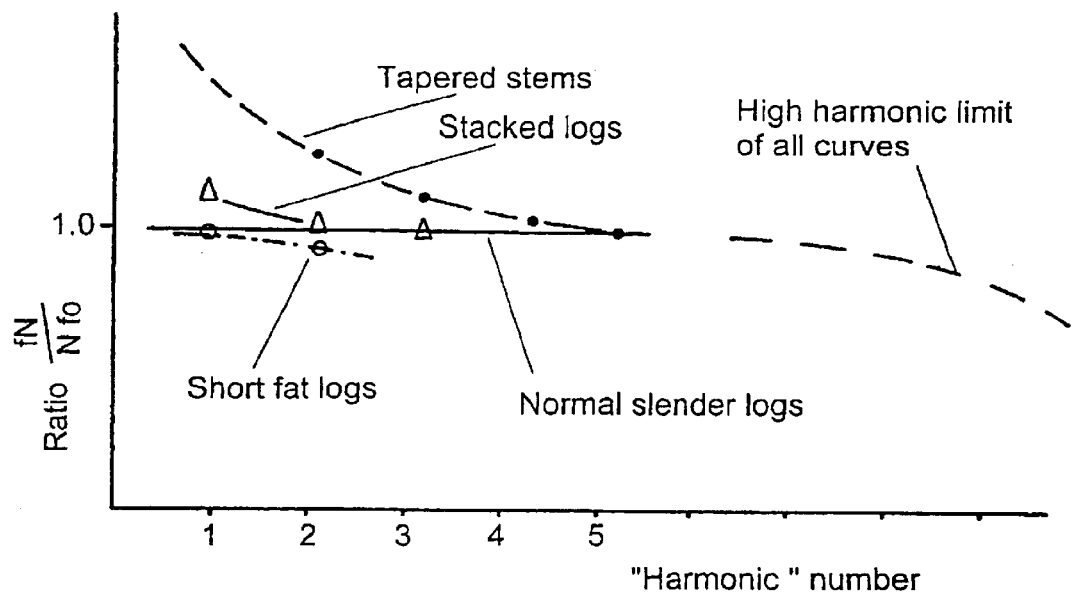
Figure 3:
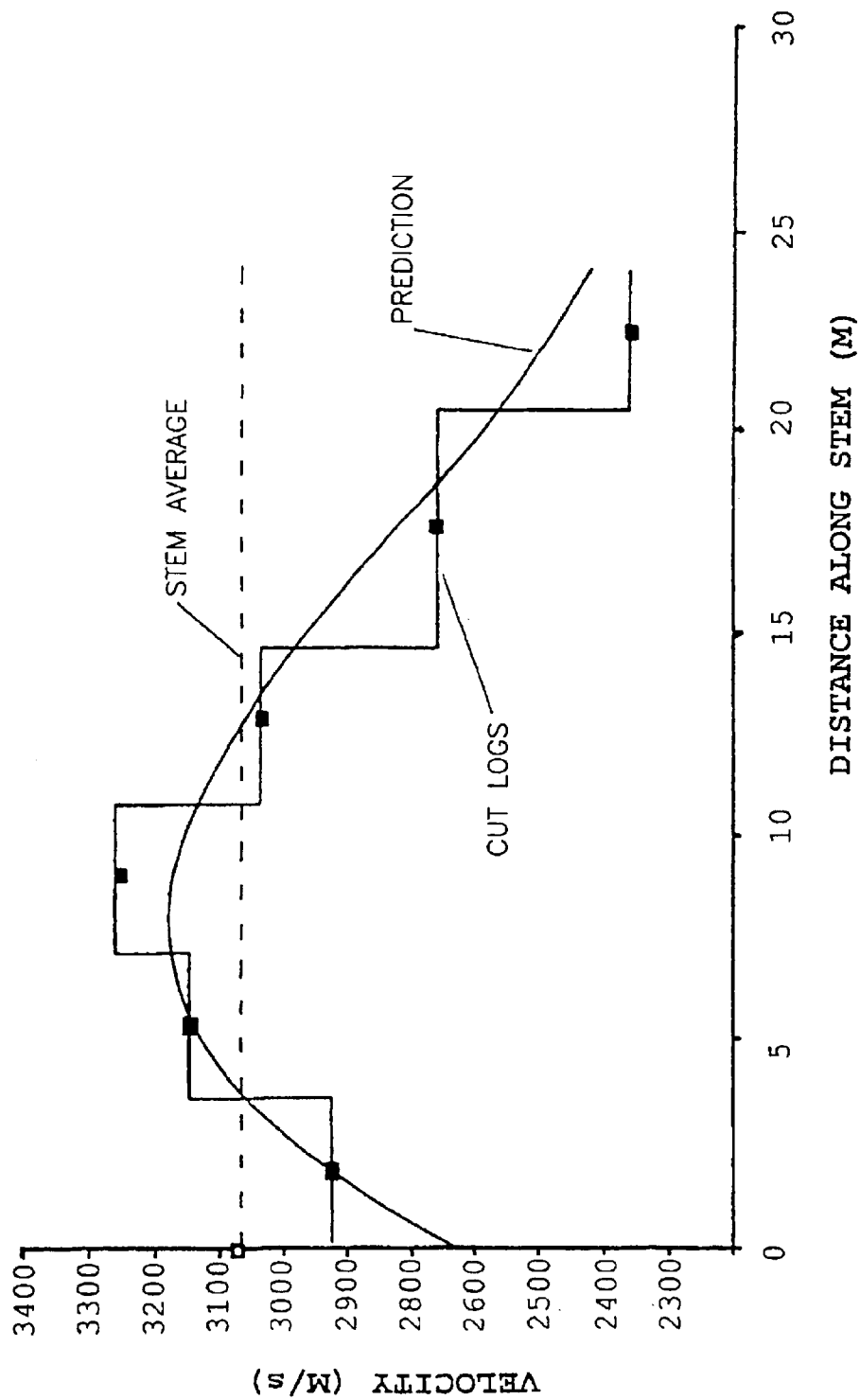
Figure 4:
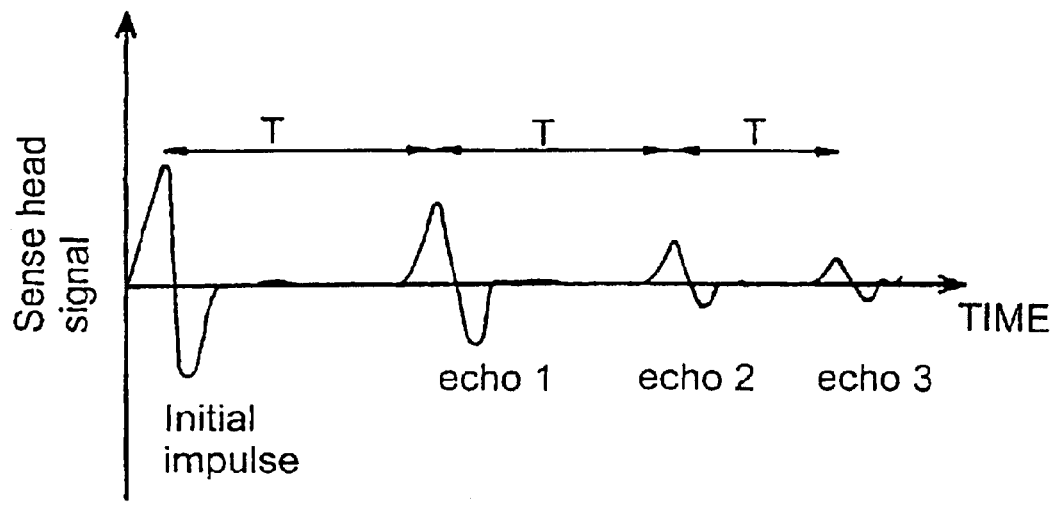
Figure 5:
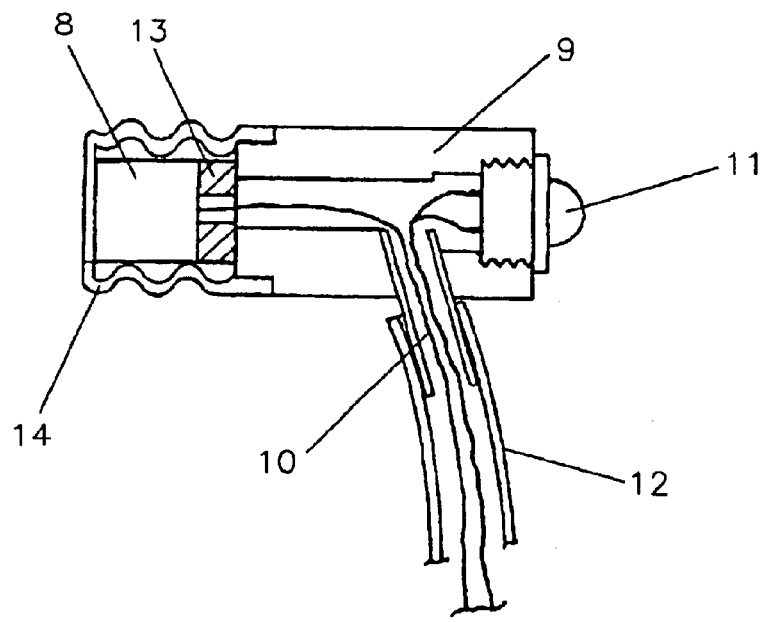
Figure 6:
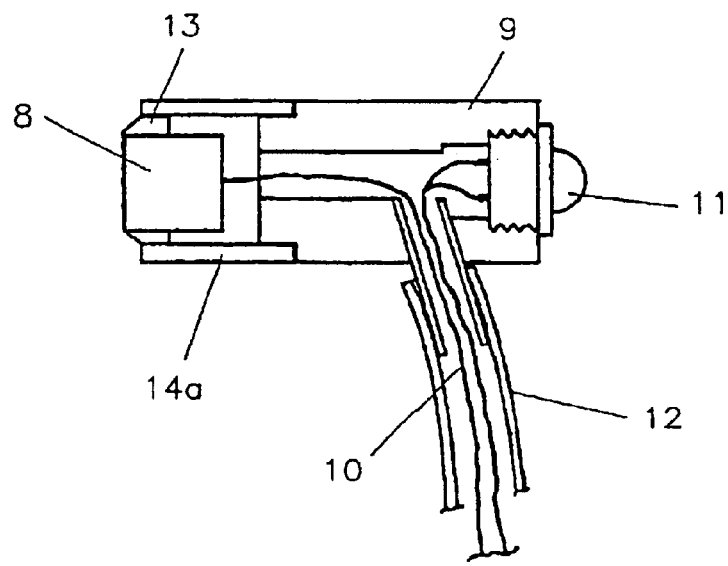
Figure 7:
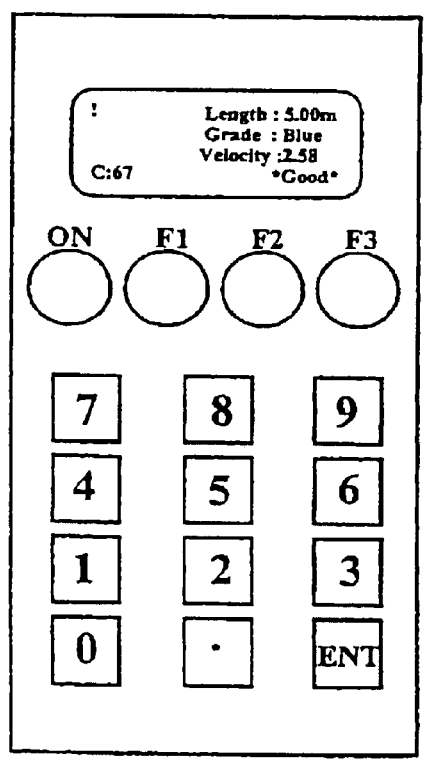
Figure 8:
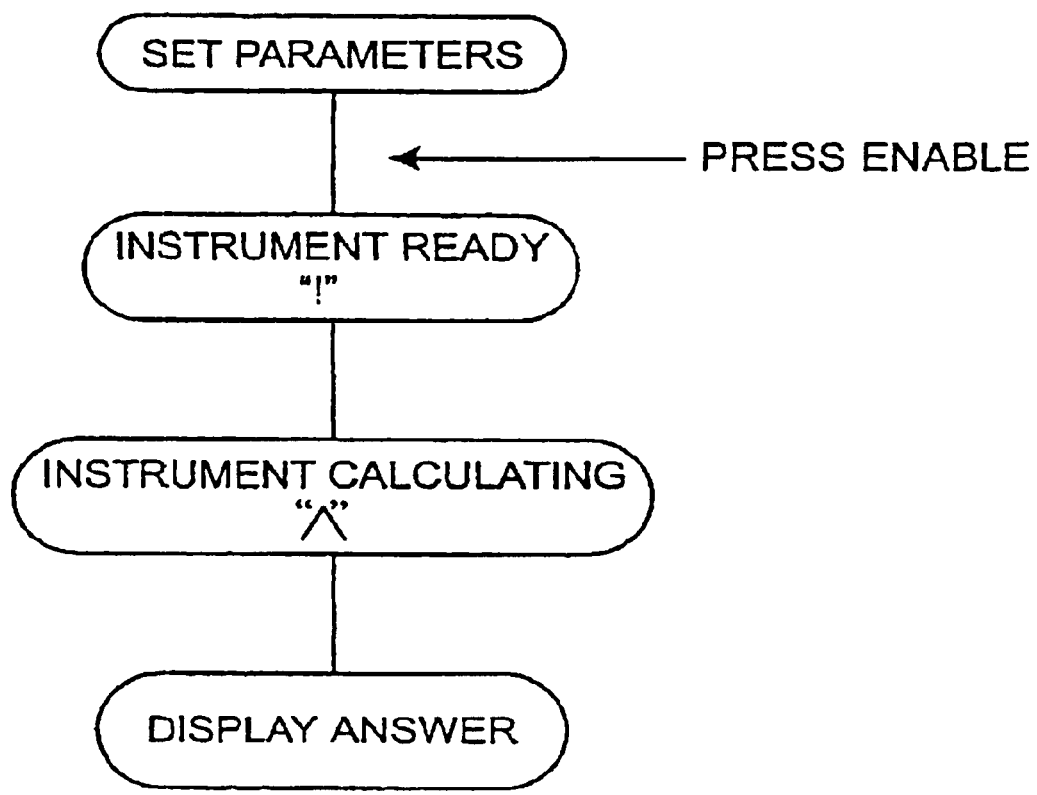
Figure 9:
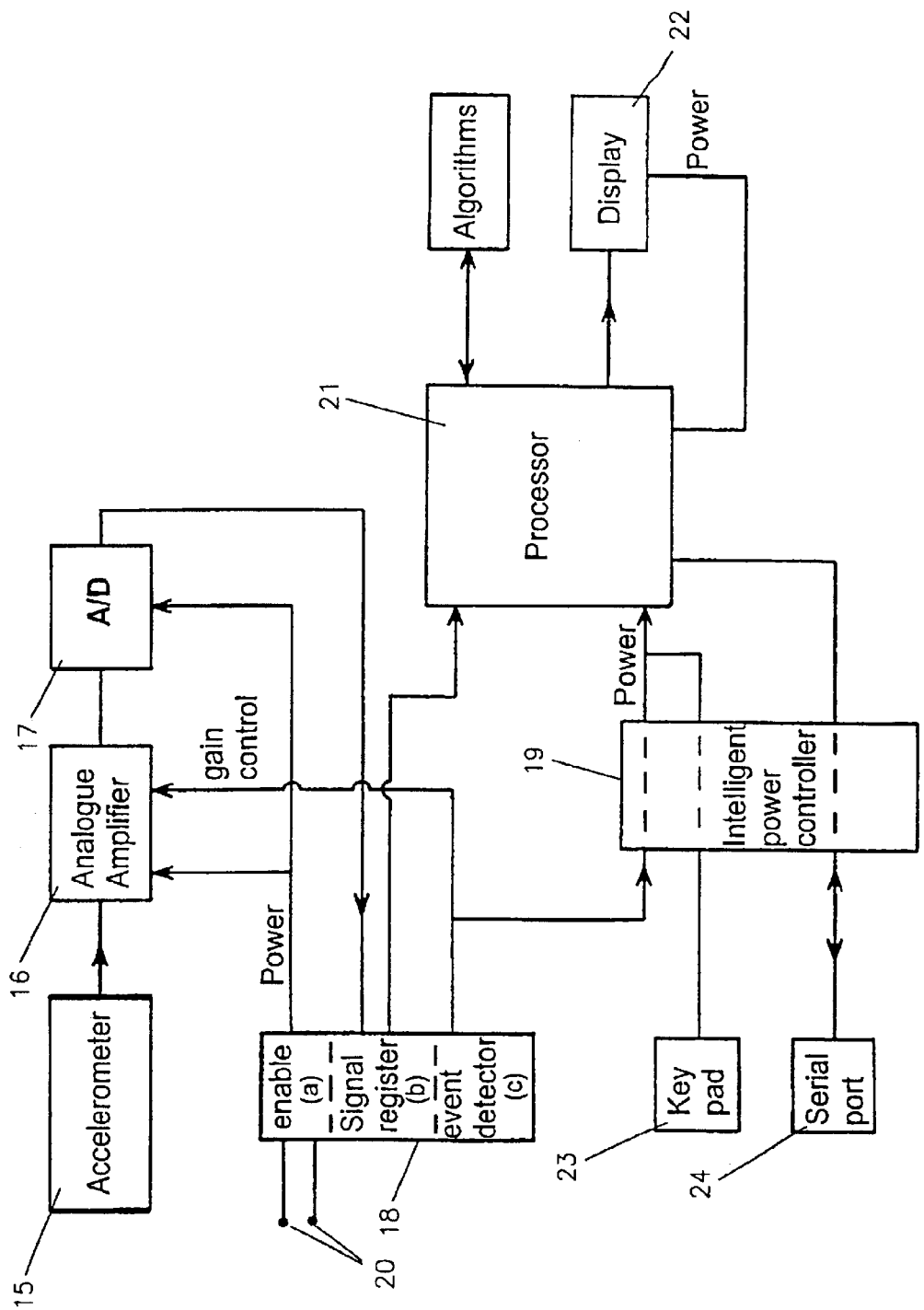
Figure 10:
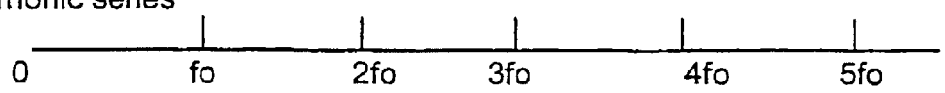
Figure 10:
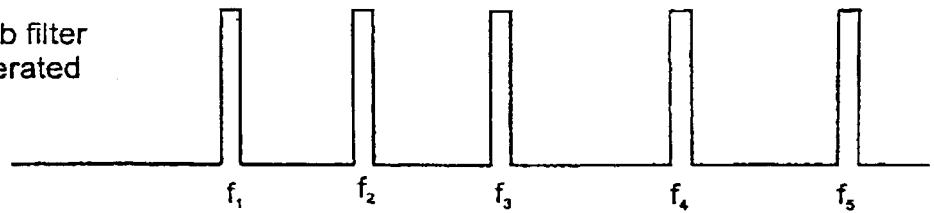
Figure 10:
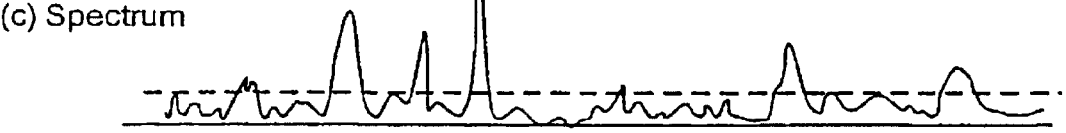
Figure 10:

Preferred forms of the present invention will now be described with reference to the accompanying drawings in which:

FIG. 1 shows a measuring instrument including an accelerometer sense head as it is preferable used against a log end in conjunction with a hammer and data interpretation devices to yield such as result to be used, FIG. 2 illustrates schematically the types of spectra derived from long and short stems, where the harmonic or overtone frequencies $f_N$ (normalised to N times the fundamental frequency $f_0$ which relates to wave speed within the log), are plotted against harmonic or overtone number, N, FIG. 3 illustrates how whole stem velocity information, combined with a knowledge of typical velocity profiles along a stem, can predict velocities within logs subsequently cut from the stem, FIG. 4 shows echo decay, FIGS. 5 and 6 shows two preferred sensing heads, FIG. 7 shows a preferred control panel FIG. 8 shows a flow chart of the measuring operation, FIG. 9 is a block diagram of the preferred electronic hardware, FIG. 10 is an illustration of the operation of a comb filter on a power spectrum, and FIGS. 11 to 15 are graphs referred to further below in the description of a trial carried out to determine wood fibre characteristics using the instrument of the invention.

Measurements carried out by us on wood as it is dried from the green to dry state have shown that there is good agreement between the static bending modulus and the so-called dynamic MOE found from the formula $$MOE = \rho V^2$$

where V is the velocity of longitudinal waves along the log or beam and $\rho$ is the mass density of the wood, including its water content. This agreement is possibly because the effective measurement frequency is low (hundreds of Hz) rather than in the ultrasonic range often reported in the literature. Ultrasonic measurements show a water-dependent modulus. The low frequency agreement has profound significance for the log or timber industry; since the density of green wood is known to be about 1000 kg/m³, regardless of the dry density. The modulus can therefore be estimated from a green velocity measurement alone. The dry value can be estimated as being perhaps 15% above this as the wood cellulose dries from saturation to equilibrium water content.

This document deals with three elements required in combination to make a fast yet portable field instrument by identification of impact-induced resonances found by Fourier analysis. Accurate measurement of the sonic velocity of logs or stems can be made in a time of a second from these resonances and a good estimate of the stiffness modulus found. The three elements are the measuring head, the signal acquisition and processing hardware, and the algorithms needed to interpret the resonance data.

In this respect see FIG. 1.

General Instrument Requirements

The requirements for a portable, hand-held tool for log assessment, able to be used by a single operator in a yard or forest are Low right and small size Ease of operation in obtaining the measurement Fast processing and display of answer, e.g. a second.

Low battery drain, e.g. operation for at least one shift on a battery

Rugged construction with a degree of waterproofing.

Robust processing algorithms able to handle variable quality data

Low cost if many units are to be deployed by technically unskilled operators

Some of these requirements are potentially contradictory, such as ruggedized but lightweight construction, fast processing but small current drain. In particular, though small "laptop" style computers are available, it is unlikely that waterproofing, full shift operation and low cost can be easily achieved. It is generally more efficient to use dedicated hardware which incorporates the analogue signal acquisition, its digitization and processing into a characteristic spectrum, further software algorithms to interpret the data, and a small, low power display rather than the full screen of a computer. Such a configuration allows major savings of power, as will be described.

Sensing Head

FIGS. 6 and 7 show two sensing heads (1), comprising a piezo-style accelerometer 8 mounted on a body 9 which contains a cable entry 10 for the wires to the accelerometer 8, and an enabling switch 11. The accelerometer is of a type which responds only to accelerations along the axis of the body. The wires are further protected mechanically by flexible tubing 12 which also prevents water ingress to the head 1 and which extends to the electronic unit (4, 5, 6) to be described.

The frequency response of the accelerometer may be chosen for the nature of the log expected. For normal forest work, a frequency response of 10 to 3000 Hz is adequate, but wider ranges may be advantageously used, particularly if the instrument is to be used in research applications.

It is preferable that the accelerometer incorporates a charge amplifier, since connection to the electronic unit may then be made through a cable of any length. The purpose of the switch 11 is to activate the signal acquisition circuits immediately prior to striking the log under test. It is desirable that the accelerometer is compliantly mounted on the body, for example on a pad of silicone rubber 13, as this enables the operator to press the head against the timber face of a log or stem end (e.g. of log 2) and maintain good contact independently of any hand movement. If the accelerometer mount is rigid, spurious acceleration signals may be generated if the flat face of the accelerometer is inadvertently rocked against the timber. In FIG. 5, a thin cap 14 of material such as neoprene rubber is fixed over the end of the head so as to be in contact with the accelerometer end face. The purposes of this is to provide some protection for the accelerometer against inevitable build up of debris such as resin from the logs under test. The cap may be cleaned or replaced. Tests have shown that 1 mm of a hard rubber only slightly impairs collection of acoustic signals from logs.

In FIG. 6, maximum sensitivity is gained at the cost of debris protection by replacing the cap 14 with a rigid tube 14a, within which the sensor 8 is directly mounted.

To take a measurement, it is sufficient to press the assembly against the end face of the log 2, depress the switch 11 (an action designed to encourage pressure contact with the timber) and strike the timber clearly but not forcefully with a mallet or hammer 3. Pressure contact must be maintained for up to half a second while the sound waves within the log decay.

Signals may be collected reliably with this head 1 regardless of the nature of the cross-cut face; for example, the deep ridges produced by the hydraulic saws in automatic harvesters such as the WARRATAH™ GENERATE signals no different from more even surfaces. It is not necessary to embed the detector in the wood to achieve coupling, a fact that considerably speeds up the sounding operation. Experience has shown that neither placement of the head or the blow is critical. This is understandable since the system analyses many tens of reflections of the acoustic pulse in modes which incorporate the entire log, so the precise nature of the initial shock becomes unimportant. This is in clear distinction from so-called stress wave testers, where a single transit time of an acoustic pulse is measured. Clearly, for stress wave testers, the initial development of the pulse from a hammer-generated, localised, near spherical disturbance, to a mode filling the log may be a significant fraction of the first transit. Nevertheless, good practice seems to be to place both the head and position the blow perhaps a quarter of the distance from the log centre to the bark. Peripheral blows tend to encourage non-longitudinal oscillations of the sample, while are not wanted.

Experience shows that unskilled operators have the unshakeable belief that if modest blows produce results, then Herculean strikes must be even more effective. This tendency can be controlled by issuing a hammer of appropriate weight for the task. For logs and stems, a weight of 400 gm is adequate. For lighter samples, such as sawn and dried framing timber, lighter mallets can be used. Only on very short logs of exceptionally large diameter have heavy hammers been beneficial in exciting clean resonances.

Electronic Unit

The electronic unit is shown by reference to function in FIG. 1 as including the processing means (a combination of means 4 to electronically measure and control and means 5 to process using algorithms) and display means 6.

The two dominating considerations of this electronic unit are the high rate of decay of the signal coming from the wood, and the need to reduce power consumption as much as possible so that effectively continuous operation on small batteries for at least one shift is possible. Consideration of currents drawn by processors capable of performing the functions required here show that some automatic form of power saving is necessary.

Measurements of the attenuation of acoustic signals in wet wood show that the signal can fall by 60 dB in 0.1s, in an approximately exponential fashion. The process of Fourier analysis in this application can be thought of as a simple way of averaging the echo times of many reflections, since the fundamental frequency $f_0$ found by Fourier analysis is the inverse of the echo time T. (FIG. 4). The reception of many echoes leads to an accurate average. It is for this reason that resonance-type instruments produce more consistent answers than single transit stress-wave times. However the echo time in a long stem is typically 10 ms. To detect 20 echoes necessitates detecting signal for 200 ms, and clearly by this time the amplitude will be very low if the attenuation is 60 dB/100 ms.

To obtain useful signals for a duration of 0.1 to 0.4s, the gain of the analogue amplifier is made to increase at a constant exponential rate, for example 20 to 60 dB, over the course of the event to partially offset the natural attenuation. Amplifier offset voltages must be carefully controlled with such a strategy to prevent dc contamination of the final spectrum. In conjunction with this, high resolution A/D converters, typically 14 bits, are used so that useful resolution can still be obtained where the signal has fallen into the microvolt range (but is still above the noise background). If the initial acoustic signal is converted to a 3V amplitude signal, the level 100 ms after this might be 3 mV, which would give some resolution on a 14 bit converter set to 3V scale, since the least significant bit is 0.19 mvolt. However, signals beyond the 100 ms time frame would quickly fail to be digitized.

The provision of time-dependent gain is vital to extend the period over which signals can be usefully digitized. 20 dB of gain over the 100 ms described above would raise the signal at that time to 30 mv, enabling the time of useful digitization to be considerably extended.

FIG. 7 shows a possible layout of the controls seen by the operator. Upon turn on, the results from the analysis of the last log are shown in the display. Should new control information be required, it is entered via the keyboard in conjunction with the Function keys F1 to F3. The most common user-information needed is a new log length if this is different from the already displayed, and this is achieved by pressing F1 and entering the new length via the key pad. The key F2 is used to select predefined log lengths to speed up entry when a few fixed lengths are expected. These lengths can have been pre-loaded into the device (using F3), and are selected by pressing F2 followed by the one of keys 0–9. The F3 key is used less frequently and in conjunction with particular key pad numbers, for example by supervisors to set up various defaults such as the maximum velocity expected, to download information to another device, read battery voltage, set default log lengths, or to allow the instrument to be controlled from an external computer.

The display shows the current length, the grade or code for the log based on its velocity, and the actual velocity. The bottom line indicates a "c" or confidence value, summarized as "*good*" or "*rehit*" based on the value. In the absence of a visual display of the spectrum, or indeed a skilled operator capable of judging from such a display that the automatically extracted velocity is the correct one, some indicator of how well the data collected fits expectations is very important. How the parameter c is calculated is described later. The value of c at which the display changes from "good to "rehit" can be changed using the F3 key.

The display shows instrument status in the top left corner. When the enable switch 11 on the head is depressed, the symbol "!" appears when the device is ready. This changes to "^" when a hit has been detected, and calculation is proceeding. The symbol "*" is used to indicate that data is being downloaded to an external device, making the instrument temporarily unavailable for new measurement.

The operator flow described above is summarised in FIG. 8.

A more detailed understanding if the invention comes from the block diagram of the electronic hardware drawn in FIG. 9. The accelerometer 15 is coupled to an analogue amplifier 16 which incorporates a gain control function. The state of the entire instrument is controlled by two programmable logic devices numbered 18 (the event controller) and 19 (the intelligent power controller). When powered up, only parts of these PLDs are operative, and since they are not switching, standing current is very low. When the enable switch 20 on the head is closed the PLD 18(a) turns on the Analogue section 16 and the A/D converter 17, and digitized samples from the accelerometer are fed to the signal register 18(b) in the PLD. If the signal exceeds a threshold, the event detector 18(c) assumes that the log or sample has been struck. The event starts the logarithmic increase in the analogue amplifier gain, and initiates the Intelligent Power Controller PLD 5, which powers up the microprocessor 21.

The microprocessor 21 records a number of digitized values over an ensuing time. Typically, 2048 readings will be taken over 400 ms, following which the analogue amplifier and A/D converter are turned off. The data are then Fourier transformed following appropriate windowing and filtering. The particular data record described combination will yield a maximum frequency of 2.5 kHz with a resolution of 2.5 Hz, which suits forest applications, but could be changed to suit other needs.

The power spectrum is then analysed by the processor 21 using algorithms discussed in the next section to extract a fundamental resonance $f_0$, and an answer displayed in the liquid crystal unit 22. This can consist of a single value for velocity, (assuming a prior log length has been entered into the unit), using the formula $$V = 2f_0 L$$

where L is the length, or the value can be converted to a speed class, and the code for that class displayed, for example "green" to indicate a colour marker to be used.

Having initiated the display, the microprocessor returns to hibernation mode to save current, and reactivates after a time of for example 30s to turn the display off under the control of the intelligent power controller 19.

It is necessary to manually enter some information, for example new log lengths. Operation of the key pad 23 is detected by the power controller PLD 19, which activates the processor 21 long enough to store the new data.

The unit is configured to deliver the minimum necessary information to operating crews, but clearly the full detail of spectral information, which may be required for R and D operations, is potentially available. The logic of the controller 19 is configured so that by keyboard entries, it is possible to send the spectral information via serial port 24 to an external computer for graphical display or data recording. Conversely, data received at the serial port activates the power controller and thence the processor, so that the serial port can be used to control the operation of the device from an external computer.

Spectrum Interpretation

It is well known that exciting a beam or log of wood into longitudinal oscillation produces a disturbance which can be Fourier analysed into a series which is harmonic, and in which the speed of sound in the wood is given by $$V = 2L f_0$$

V is the speed of longitudinal compressional motions along the member, and since the lateral boundaries are stress free, is given by the well known relation $$V^2 = E/\rho$$

where E is Young's modulus, and $\rho$ the material density.

In samples of regular cross section, particularly where the these are slender, higher resonances are closely harmonically related to the fundamental. Extraction of the modulus using the two equations above is simple since the fundamental is easily identified. The number of harmonics detected depends on the frequency characteristics of the exciting impulse. Wet wood is soft. Typically a hammer is arrested in a time of the order of a millisecond and the spectra cannot be expected to contain harmonics greatly in excess of the inverse of this time, i.e. greatly above 1 kHz. However, modelling studies we have made show that slenderness of the beam is a factor also. Thin beams or logs encourage the excitation of high harmonics, while short fat beams or logs do not.

In practice, there is a variety of circumstances where this picture requires modification to extract reliable values of the modulus.

In field use, samples may not be slender—a four metre saw log with a diameter of 50 cm is considerably "fatter" than a sawn beam 100 by 50 mm, and because of the excitation spectrum and the log shape, few harmonics will be detected in the log compared with the sawn wood. A decision on which frequency should be identified as the fundamental may be less clear for the log. We have found that this can be exacerbated by the presence of unwanted noise spikes in the spectrum, or unwanted resonances arising from less than optimum hammer blows. Situations of poor spectra have been found to be inevitable in some physical locations, for example when obtaining spectra from the logs of cross-cut stems, when the log faces are relatively inaccessible. In development work, it is possible to repeatedly take a spectrum until by chance it is "clean". In a production tool, a high success rate in analysis must be available, and a built-in indication of the confidence in the answer is desirable.

It is also recorded in the literature that spectra from logs in stacks may differ from harmonic. We have observed that the fundamental can be typically 5% higher than the value expected from the resonance identified as the second harmonic, and values of 10% have been seen. Calculating MOE based on the fundamental or the second harmonic in this case would have a discrepancy of 20%, which is unacceptable.

Tests done on logs measured first in a stack and then unstacked on bearers show that it is the fundamental which is shifted most. The second harmonic is affected by about 1% by stacking effects, and higher harmonics, where seen, are approximately unchanged. As a rough guide, the second harmonic is a more reliable estimate of stiffness than the fundamental. Always, any frequency shift of the fundamental is positive.

However, some short logs, measured in isolation on bearers, still show a small but measurable departure from a harmonic series, usually with the higher harmonics at frequencies below what would be expected.

In the case of stems, the departure can be enormous. Since stems are "slender" many harmonics can be excited in the region below 1000 Hz, and the lowest member of the series, if the fundamental, has been observed to be as much as 40% above the value implied by the higher harmonics. This would lead to a difference of two in the predicted value of stiffness.

All the foregoing situations must be allowed for in the analysis software.

Finite Element modelling of the eigenmodes of the logs and stems has been carried out to gain an understanding of the factors involved in departures from harmonic series.

The results show that for a cylindrical log, the lowest resonance frequencies are closely harmonic. This remains true when the anisotropic elasticity of wood is included. The frequency of the fundamental mode is only slightly affected by the value chosen for Poisson's Ratio, which is fortunate since this parameter is ill-defined in wood. Further, no evidence was found that radial structure in logs, approximated by an inner core of low stiffness surrounded by a stiffer outer cylinder produced other than some average spectrum of the two; i.e. such internal structure is not responsible for anharmonic effects.

At a frequency when the wavelength across the log approaches the wood diameter, the longitudinal frequencies become lower than expected i.e. a harmonic pull-down of the kind described earlier i seen. Due to the fact that the sound speed across the log is of the order of one tenth the longitudinal speed, this condition may be reached at what may be surprisingly low harmonic numbers in "fat" logs. Model results showed that ill-defined body resonances prevailed at higher frequencies. In other words, the spectra of short fat logs might be expected to show a small lowering of higher harmonics compared to the fundamental, but few harmonics will be seen. This roughly accords with our observational experience. The theory shows that for non-tapering logs, not stacked, the best indication of stiffness comes from the fundamental.

The situation for stems is different because of their taper. Taper is the only parameter found which causes the resonances following the fundamental to be sharply lowered in frequency. However, the modelling shows that it is the low harmonics which are raised above the value expected from the wood modulus, while the high harmonics still indicate stem stiffness. As with non-tapered logs, when the transverse wavelength of a resonance frequency approaches the stem diameter, the harmonic frequency tends to fall lower than expected. Because for stems, the frequency at which this is predicted to occur is high, the effect is unlikely to be seen and indeed we have not observed it.

Tapered-log modelling shows that it is the taper per wavelength which is important. The imbalance or asymmetry occurring in the oscillating mass and spring forces about each node in the log is the underlying cause of frequency shift. Thus the fundamental mode, where the stem is half a wavelength long, can be strongly affected. The taper per wavelength in the $N^{th}$ harmonic is only $1/N$ of that in the fundamental. The higher harmonics are much less affected by the taper and yield the correct stiffness. Modelling shows, and our experience confirms, that to a reasonable approximation, if the fundamental resonance frequency is raised by a factor $ke^{-1}$ over its value expected on the basis of the stem length and stiffness, the $N^{th}$ harmonic will be raised by a factor $ke^{-N}$ over its harmonic value. Resonances therefore fairly quickly reach their harmonic values. Other expressions which express the deviation of the overtones from a harmonic series can be derived.

We believe that the cause of the rise in the fundamental resonance of stacked logs noted earlier also lies in asymmetry similar to the case of the tapered stem. Now, the effect is that a log may be pinned to its neighbour in only two or three places. For low harmonics, this can produce a major elastic asymmetry and consequent lifting of the fundamental. Most of the nodal sections of the higher harmonics will not see the pinning points and their frequencies will be little affected.

The various cases described are illustrated in FIG. 2, where $f_N$ is the frequency of the $N^{th}$ member of the actual resonance series, and $f_0$ is the "true" fundamental, or lowest member of the series, from which the velocity and stiffness can be found. The lowest member $f_1$ coincides with $f_0$ if the long is slender and non-tapered, but there may be no resonance energy seen at $f_0$, for example with stem spectra.

This background of observation and modelling results provides the basis of the algorithms used to analyse spectra. While a velocity can be judged by an operator from a screen display of spectra, an automatic system needs to allow for noise peaks, non harmonic effects, and perhaps most confusing to an automatic process, missing spectral peaks which confuse the identification of a series.

The algorithm must reject occasional noise peaks in the spectrum, which means that as many as possible of the resonant peaks should be identified, since random noise spikes will not occur in harmonics ratios. It must allow for the fact that frequencies may be non-harmonic to a small extent in short logs and greatly so in stems and it should not require all members of a series to be present.

The identification system first considers only spectral signals above a threshold, for example those within 20% of the power of the largest spectral peak. It may be advantageous to smooth data in the frequency domain before doing this if signals are noisy to limit the number of peaks to be considered.

Given the length of a log and a likely range of sound speed, the possible range of frequencies for a fundamental is calculated and spectral peaks sought within the that range. The search is done within velocity windows whose ranges are less than 2:1. Within such a window, the range of possible fundamental frequencies cannot overlap the consequent second harmonics range, and so allows fundamental and second harmonic to be distinguished. If no successful identification is ultimately made within this window, subsequent searches are made within modified velocity windows. This is generally not required. Most green *P. radiata* logs have velocities between 2.5 and 4 km/s which fulfills the velocity criterion.

For each potential candidate for a fundamental resonance, a filter comb is constructed. For example, if the peak to be tested had a frequency of 300 Hz, a comb consisting of 300, 600, 900, Hz is constructed, and the energy measured within that comb by adding the power at the comb frequencies. For short logs, a deviation of a few percent is allowed, i.e. energy is considered to be part of the comb if it falls within a predetermined band about the expected centre, to take account of the effects described earlier which are encountered in practice.

A useful variation of this procedure, which takes into account the stacking effect, is to base the comb search on the second harmonic, since this is relatively little affected by stacking, and to allow deviations from harmonic to fall mainly at the fundamental frequency. The velocity, and modulus, are then calculated from the second harmonic by assuming that this is the frequency $2f_0$.

This procedure is repeated for all peaks which are candidates for the fundamental within its allowed frequency range. The preferred identification is that spectral peak whose comb accounts for the greatest quantity of spectrum power. A numerical confidence measure which follows from this procedure is the ratio of the power accounted for in the peaks within the comb to the sum of power in other peaks plus the background noise level.

In the search to identify harmonic members, no power is considered in peaks which fall at frequencies which would lead to impossibly low velocities. The reason for this is that such peaks can be generated by moving the accelerometer head during the course of recording data. Nevertheless, their inclusion in the confidence measure gives operator warning that such an event might have happened.

It will be occasionally found, particularly with short "fat" logs, that only one resonance is seen. In that case, provided it produces a plausible velocity, it must be assumed to be the fundamental.

The procedure is modified for stems where taper is important resulting in a grossly non-harmonic series. A range of fundamental frequencies is sought as before, but the comb generated is considerably modified. Because the procedure is more complex and suits the presence of many harmonics, it is only applied to logs above a preset length, for example 12 m.

It $f_0$ is as before the "true" fundamental from which the speed in the tapered log can be found and the modulus calculated, the exponential deviation from a harmonic series described earlier can be expressed as $$(fN - Nf_0)/fN = ke^{-N}$$

Here fN is the frequency of the $N^{th}$ harmonic, and k is a constant between 0 and 1, which must be determined. Other expressions are possible. One such alternative expression has the form $$f_N/Nf_0 - 1 = (\text{constant})/N^2$$

When for example using the former expression, having identified one peak as a possible fundamental (i.e. N=1), for a given value of k, a value of $f_0$ is defined, and a comb of frequencies can then be generated at which the other harmonics should fall. The power falling within the comb is summed as before, and the procedure repeated with different values of k to find the optimum match for that presumed fundamental mode.

The comb filter process is illustrated in FIG. 10, with reference to the analysis of a stem, using the exponential expression above to analyse the spectrum sketched in FIG. 10 panel (c). This spectrum shows a noise floor, from which a genuine resonance sequence occurs near the frequencies $f_1$, $f_2$, $f_4$ and $f_5$, but the member $f_3$ is missing and there is a noise pulse or unwanted resonance mode between $f_1$ and $f_2$. To test whether $f_1$ is indeed the first member of series, value $f_0$ is chosen, which defines the harmonic series $nf_0$ in FIG. 10(a) and the value of k. This frequency $f_0$ is that which, together with the stem length, defines the true wave propagation speed sought. A series of displaced frequencies $f_1$, $f_2$ . . . which are the centre frequencies of the comb filter can now be generated from the exponential expression. Passbands for the filter are created by opening narrow windows about these centre frequencies, thus defining the comb filter shown in FIG. 10(b). The power spectrum in FIG. 10(c), minus a threshold representing the noise floor, is multiplied by the filter to yield the output of FIG. 10(d), which is the spectral power falling in the windows of the comb. The sum of the power coming through the filter is a measure of how well the original harmonic series describes the actual spectrum. A range of values of $f_0$ and k are tested to find the combination which produces the best fit. Note that the noise spike between $f_1$ and $f_2$ is ignored, and the absence of the third overtone is merely regrettable, not catastrophic, in generating a fit.

This procedure will sometimes yield two values of k which generate equal summed powers. A second measure is therefore taken at each value of k to express how closely the comb is fitted. This is the sum of the deviations of each peak from its comb centre frequency. The choice is made on the basis of the most power and the best comb fit.

The next candidate resonance for the fundamental is then tested, and classed as a better identification or not on the basis of both the resonance power accounted for, and the closeness of fit to the comb. With a fast processor, computation time is acceptably short.

In effect, a transformation is being done to best fit the given resonance to a harmonic set, and does not require all member of a series to be present. It could begin by generating a comb by assuming that a particular peak was the $N^{th}$ harmonic and generating a comb from that. In fact, the algorithm does this, testing each peak in turn to be a particular harmonic of an assumed series, and finding the goodness-of-fit for each combination. This is useful since some stem signatures have an ill-defined fundamental frequency.

The complexity of these procedures is frequently not needed because many resonance spectra have an obvious interpretation. Their need is in the general case, when a reliable answer is needed in a high percentage of cases from less than perfect data, and the data itself must be used to indicate to unskilled operators whether or not the answer is reliable.

Stem average velocities can be advantageously used to more intelligently break stems into logs. We have found that the velocity varies along stems in a broadly similar way and can be predicted.

It can be represented by a sum of a cubic expression involving the position along the stem and a constant term. With reference to FIG. 3, a constant term in the cubic can be adjusted by calculation so that the transit time derived by integrating the speeds from the cubic expressions along an actual stem equals the time found from the averaged velocity V along the stem. For example, $Ax^3+Bx^3+Cx+D$ where x is the distance along the stem and A, B, C and D are constants.

The curve drawn is the resulting prediction of speed along that stem. Also shown in FIG. 3 as the stepped line are speeds subsequently measured in the sequence of logs made from that stem. Clearly in this example, a combination of reference information and stem-average measurement has enabled a considerable improvement to be made in velocity or stiffness estimation along the stem prior to making cuts.

A better non cubic predictive model might be of the form $$V/_{VT}=aL^b{}_M(1-L_M)^a+d$$

where a, b, c and d are constants,

V is velocity of the log $V_\tau$ is velocity of the tree stem from which the log is to be derived, and $L_M$ is the mid-point relative length of the log.

Data such as that in FIG. 3 gives confidence in the comb filter technique. Generally, the transit time deduced for a stem based on a determination of $f_0$ agrees within about 1 to 2% with the sum of the transit times in each log cut from that stem, each of which has been analysed by a comb filter. This agreement is very satisfactory. A speed based on the lowest resonant frequency in a stem, and simple interpretations of the log spectra, could not approach such accuracy.

Stiffness measurement is a parameter which has had recent prominence, both in regard to log and timber stiffness and the implications it has for the basic constituent fibres of the wood. Measurement of stiffness using so-called stress wave timers, that is to say electronic instruments which detect the time of flight of a sonic impulse along or across a piece of wood have been in use for many years. While it is generally accepted that they measure a quantity indicative of mechanical stiffness, for forest use, they tend to be of marginal accuracy, and relatively insensitive (due their inherent broadband nature) and therefore difficult or impossible to apply to long logs. Their fatal flaw is that they require double ended operation, i.e. detectors need to be placed at each end of the log under test. Logistically, this is unacceptable in forest use.

In 1986, Sobue demonstrated the excitation of longitudinal resonances from a log or beam which had been struck by a hammer, their detection by a single sensor, and their identification by Fourier analysis. However this process was well understood as a general analysis method in material analysis prior to that time. This development however demonstrated that single-ended testing of logs to obtain an indication of stiffness modulus was possible. In general, subsequent developments have used commercial elements such as spectrum analysers, or standard computers, which mean that true field-portability has not been achieved and it has not been possible to survey production quantities of timber.

The following describes a trail carried out to test use of the instrument of the invention for determining wood fibre characteristics. The objective of the trail was to segregate 5000 pulp logs into three classes and process each through a commercial continuous digester and evaluate the properties of the pulp which is produced.

Trial Description 5000 pulp logs were tested for sound speed transmission using the instrument of the invention described above. The logs were separated into three different classes based on sound speed:

Slow: velocity <2.80 km/s

Medium: 2.80 ≤velocity <3.30 km/s

Fast: velocity ≦3.30 km/s

The logs in each class were then chipped and processed through a 800 tonne/day Kamyr continuous digester. The three classes were processed sequentially through the digester.

Dried pulp samples were collected every 20 minutes from the Pulp Dryer while the trail was in progress. Samples of chips from the exit of the chipping plant were also collected as each sound class was being processed.

Length Weighted Fibre Length (LWFL) was measured with a Kajaani FS200 fibre analyser. Pulps were refined in the PFI Mill for 1000 revolutions and standard hand sheets prepared according to appropriate Appita standard methods. Wet Zero Span Tensile Strength (WZST) was measured with a Pulmac TS100 Tensile Tester and other hand sheet properties were measured according to Appita standards. The basic density of the chips was also measured according to the Appita standard.

Figure 11:
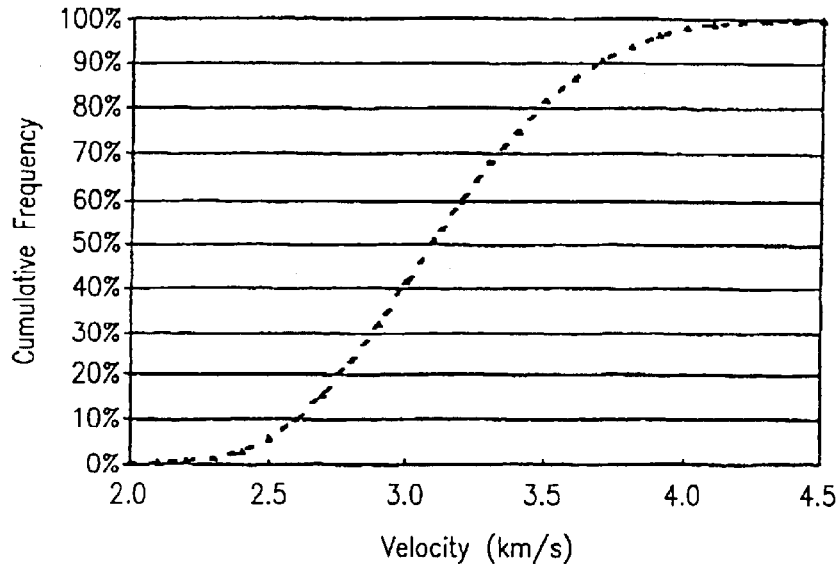
Figure 12:
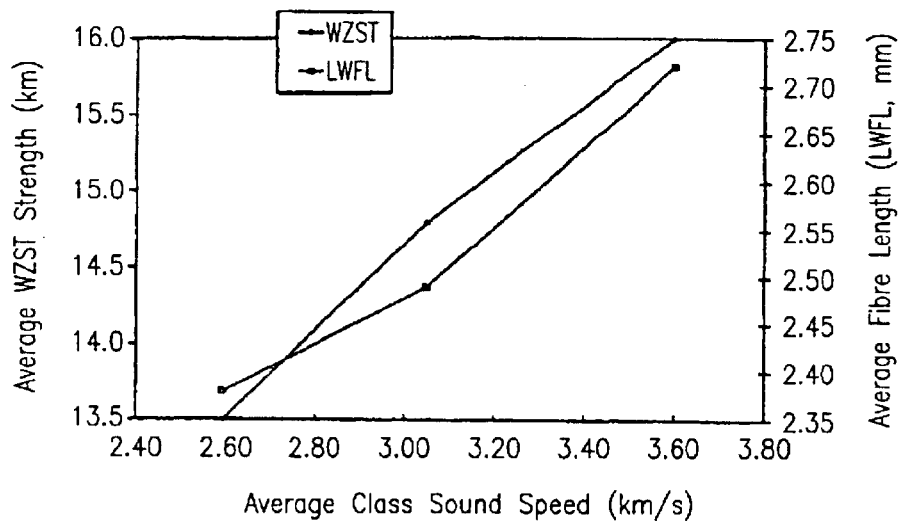
Figure 13:
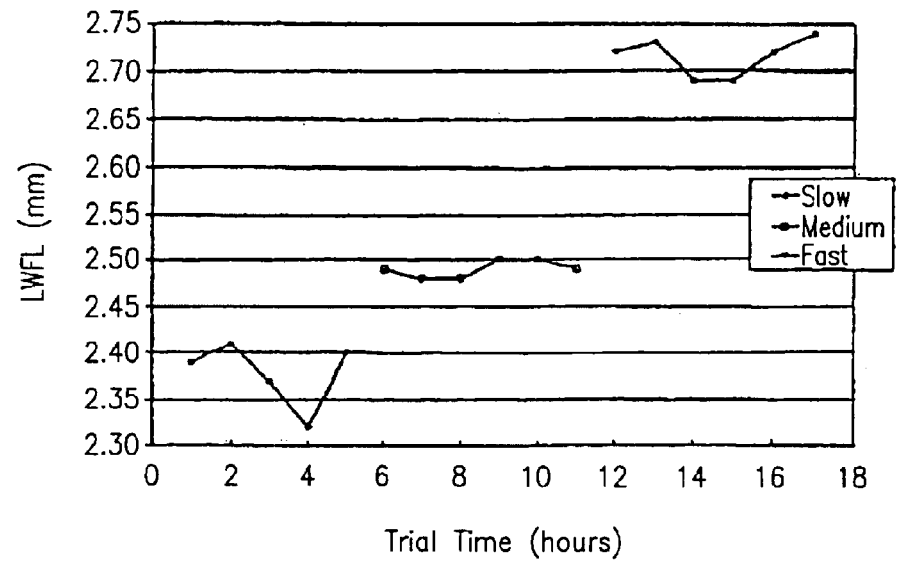
Figure 14:
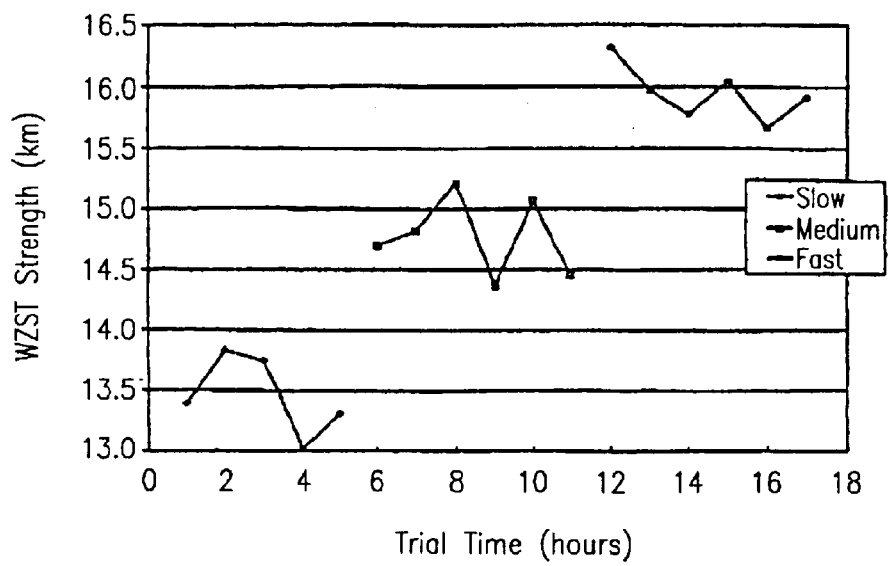
Figure 15:
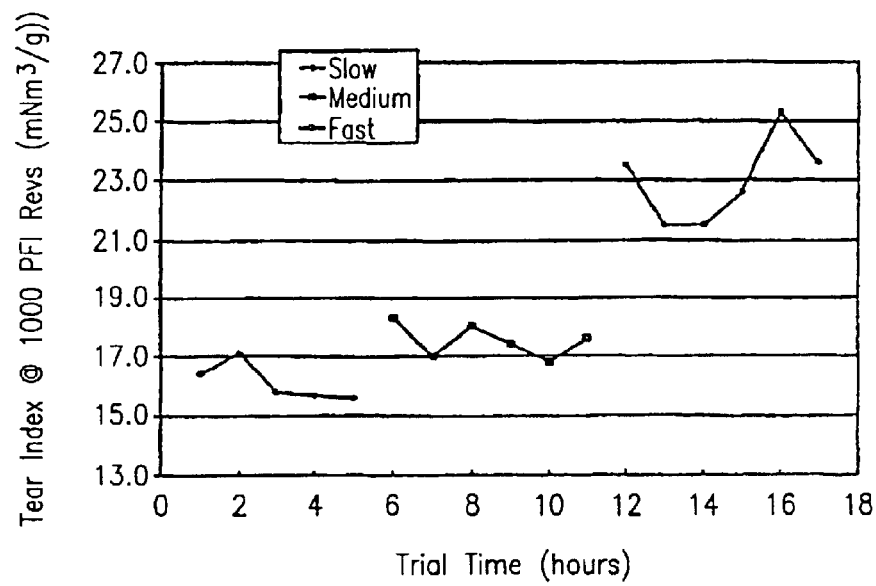

Results:

The average characteristics of the three log classes and the pulps made from each are shown in Table. FIG. 11 gives a cumulative frequency distribution for sound speed, showing that the data are normally distributed. FIG. 8 plots average pulp properties (fibre length and WZST strength) for each log class against average class sound speed. Chronological plots of fibre length, WZST strength, and Tear Index are given in FIGS. 12 to 14.

TABLE 1

Average Characteristics of the Three Log Classes and the Pulp Made from Each

| Class | Average Class Velocity (km/s) | Average Basic Density (kg/m$^3$) | Log Distribution by Class | | Average Weight/ Log (tonnes) | Average LWFL (mm) | Average WZST Strength (km) |
|---|---|---|---|---|---|---|---|
| | | | % by no. | % by wt. | | | |
| Slow | 2.59 | 389 | 23 | 34.2 | 0.72 | 2.38 | 13.5 |
| Medium | 3.05 | 400 | 45 | 43.7 | 0.49 | 2.49 | 14.8 |
| Fast | 3.80 | 429 | 32 | 22.1 | 0.33 | 2.72 | 16.0 |

Several features are apparent in these data:

average log size decreased as sound speed increased. This is an unexpected result, since small log diameter is often thought to indicates low wood density;

there is a strong relationship between average fibre length and WZST strength and average class sound speed;

average basic density correlated reasonably well with average sound speed, suggesting that when measurements for large numbers of logs are averaged, sound speed can be related to basic density;

the pulp properties obtained from the three log classes are distinctly different, which indicates that three log sorts will be commercially useful;

pulp properties are very consistent within each sound class.

Thus, log segregation has provided a useful separation of a mixed quality log supply into three, more homogeneous log groups. The pulps obtained from each log class would be suitable for different end-use applications.

What is claimed is:

1. A apparatus for providing an indicator of or from which stiffness can be estimated for logs of length L, said apparatus comprising a sensing device placed in contact with or in close proximity to a log end to detect at least part of a frequency spectrum of resonant plane acoustic waves $f_1, f_2, \ldots f_n$ resulting from an induced disturbance that travels the length L and reflects at ends thereof, said induced disturbance being causable by a striking of one of the other log end and the log end, a processing device to derive the indicator from spectral information detected by said sensing device, and a display device to display said indicator received from said processing device, and wherein L is entered into said processing device, and wherein said processing device derives, as said indicator $V^2$ and where V is the acoustic speed in a relationship MOE=density×$V^2$ by reference to both L and $f_0$, where $f_0$ is a fundamental frequency of the acoustic spectrum $f_1, f_2, \ldots f_n$ and where MOE is a dynamic modulus of elasticity, and wherein $f_0$ is derived by the processing device using a best fit spectral analysis of the resonant plane frequencies of the at least part detected acoustic spectrum $f_1, f_2, \ldots f_n$.

2. The apparatus as claimed in claim 1, wherein at least one of said sensing device and said processing device includes an amplification device to ensure a gain to ensuing echoes.

3. The apparatus as claimed in claim 1, wherein said sensing device is placed in contact with said log end.

4. The apparatus as claimed in claim 1, wherein said sensing device carries a switch for said processing device conducive, when activated, of good log/sensing device contact.

5. The apparatus as claimed in claim 1, wherein said sensing device is compliantly mounted to a sensing head to be physically pressed by a user against a log surface to be tested.

6. The apparatus as claimed in claim 5, wherein the compliant mounting of said sensing device within the sensing head, is compliantly mounted by silicone rubber.

7. The apparatus as claimed in claim 5, wherein said sensing device is in the sensing head connected by a flexible connection to an apparatus carrying said processing device and said display device.

8. The apparatus as claimed in claim 1, wherein said sensing device includes a piezo-style accelerometer.

9. The apparatus as claimed in claim 1, wherein said processing device has an analog signal acquisition device, a device for digitization and processing into a characteristic spectrum of an acquired analog signal data of echoes and further software algorithms to interpret the data.

10. The apparatus as claimed in claim 1, wherein, with a view to power saving, said display device is a small, low power display.

11. The apparatus as claimed in claim 1, wherein said sensing device is in a sensing head capable of one handed manipulation by a user and whereby power consumption is minimized by allowing initiation of a measurement sequence by finger pressure on a push switch immediately prior to striking of a log to be tested, the finger pressure on the push switch encouraging positive contact between the sensing head and a log surface.

12. The apparatus as claimed in claim 1, wherein said processing device is adapted to threshold a signal from said sensing device and immediately to apply an exponentially increasing amplification of the signal to compensate for absorption of the signal in the log so increasing the time over which acoustic signals are digitalized and to increase spectral resolution.

13. The apparatus as claimed in claim 1, wherein power consumption is adapted to be minimised by allowing operation under control of PLDs which remain in low current mode until enabled by an initiation switch after which there is a powering up of analogue functions of said processing device with respect to signal acquisition, powering up and analysis of the signals and a sending of results to the display device before being subsequently powered down after a time period.

14. The apparatus as claimed in claim 1, wherein data entries are made into said processing device by a keyboard.

15. The apparatus as claimed in claim 14, wherein preset information for data entry is selected from a class of at least one (i) velocity class codes, (ii) log length codes, (iii) information analysis purposes, (iv) information for instrument configuration purposes, and (v) to control sending the spectral information via a serial port to an external computer for graphical display or archiving.

16. The apparatus as claimed in claim 1, wherein said sensing device is adapted to be placed at or in close proximity to a same log end as a log end to be struck to provide said induced disturbance.

\* \* \* \* \*